United States Patent
Di Carlo et al.

(10) Patent No.: US 10,473,644 B2
(45) Date of Patent: Nov. 12, 2019

(54) DEVICE AND METHOD FOR FORCE PHENOTYPING OF CELLS FOR HIGH-THROUGHPUT SCREENING AND ANALYSIS

(71) Applicant: THE REGENTS OF THE UNIVERSITY OF CALIFORNIA, Oakland, CA (US)

(72) Inventors: Dino Di Carlo, Los Angeles, CA (US); Peter Tseng, Saratoga, CA (US); Ivan Pushkarsky, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/105,627

(22) Filed: Aug. 20, 2018

(65) Prior Publication Data
US 2018/0356396 A1   Dec. 13, 2018

Related U.S. Application Data

(63) Continuation of application No. 15/300,021, filed as application No. PCT/US2015/023136 on Mar. 27, 2015, now Pat. No. 10,082,497.

(Continued)

(51) Int. Cl.
*G01N 21/00* (2006.01)
*G01N 33/50* (2006.01)
(Continued)

(52) U.S. Cl.
CPC ........ *G01N 33/5026* (2013.01); *B01L 3/5085* (2013.01); *G01L 1/247* (2013.01);
(Continued)

(58) Field of Classification Search
CPC ............ G01N 33/5026; G01N 33/487; G01N 21/6458; G01N 33/582; G01N 2021/6441;
(Continued)

(56) References Cited

U.S. PATENT DOCUMENTS

2003/0032203 A1   2/2003   Sabatini et al.
2005/0264805 A1   12/2005  Cromwell et al.
(Continued)

FOREIGN PATENT DOCUMENTS

WO   2013/074972 A1   5/2013

OTHER PUBLICATIONS

PCT International Search Report for PCT/US2015/023136, Applicant: The Regents of the University of California, Form PCT/ISA/210 and 220, dated Jul. 13, 2015 (5pages).

(Continued)

*Primary Examiner* — Abdullahi Nur
(74) *Attorney, Agent, or Firm* — Vista IP Law Group LLP

(57) ABSTRACT

A system for assaying forces applied by cells includes an optically transparent substrate comprising a soft material having a Young's modulus within the range of about 3 kPa to about 100 kPa. An array of molecular patterns is disposed on a surface of the optically transparent substrate, the molecular patterns include fluorophore-conjugated patterns adherent to cells. The system includes at least one light source configured to excite the fluorophore-conjugated patterns and an imaging device configured to capture fluorescent light emitted from the fluorophore-conjugated patterns. Dimensional changes in the size of the patterns are used to determine contractile forces imparted by cells located on the patterns.

19 Claims, 12 Drawing Sheets

Related U.S. Application Data

(60) Provisional application No. 61/972,171, filed on Mar. 28, 2014.

(51) Int. Cl.
| | | |
|---|---|---|
| *G01N 33/58* | (2006.01) | |
| *G01N 21/64* | (2006.01) | |
| *G01L 1/24* | (2006.01) | |
| *B01L 3/00* | (2006.01) | |
| *G01N 33/487* | (2006.01) | |

(52) U.S. Cl.
CPC ....... *G01N 21/6458* (2013.01); *G01N 33/487* (2013.01); *G01N 33/582* (2013.01); *B01L 2300/0654* (2013.01); *B01L 2300/0829* (2013.01); *B01L 2300/168* (2013.01); *G01N 2021/6419* (2013.01); *G01N 2021/6441* (2013.01)

(58) Field of Classification Search
CPC ........... G01N 2021/6419; B01L 3/5085; B01L 2300/168; B01L 2300/0829; B01L 2300/0654; G01L 1/247; B05D 5/00; B05D 5/12; B05D 1/28; B05C 1/00
See application file for complete search history.

(56) References Cited

U.S. PATENT DOCUMENTS

| | | | |
|---|---|---|---|
| 2011/0244116 A1* | 10/2011 | Badre | B82Y 30/00 427/58 |
| 2012/0212824 A1 | 8/2012 | Sakurai | |
| 2013/0098442 A1 | 4/2013 | Ochiai et al. | |
| 2014/0024045 A1 | 1/2014 | Thery et al. | |

OTHER PUBLICATIONS

PCT Written Opinion of the International Search Authority for PCT/US2015/023136, Applicant: The Regents of the University of California, Form PCT/ISA/237, dated Jul. 13, 2015 (11pages).

Chen, Xi et al., Bacillus spores as building blocks for stimuli-responsive materials and nanogenerators, Nat Nano 9, 137-141 (2014).

Fu, Jianping et al, Mechanical regulation of cell function with geometrically modulated elastomeric substrates, Nature Methods, vol. 7, pp. 733-739, (2010).

Sniadecki, Nathan J. et al., Microfabricated Silicone Elastomeric Post Arrays for Measuring Traction Forces of Adherent Cells, Methods in Cell Biology, vol. 83 (2007).

Tseng, Qingzong et al., A new micropatterning method of soft substrates reveals that different tumorigenic signals can promote or reduce cell contraction levels, Lab Chip, 2011, 11, 2231-2240.

Wei, Qingshan et al., Fluorescent Imaging of Single Nanoparticles and Viruses on a Smart Phone, ACS Nano 7, 10, 9147-9155 (2013).

Zhu, Hongying et al., Cost-effective and compact wide-field fluorescent imaging on a cell-phone, Lab Chip, 2011, 11, 315-322.

PCT International Preliminary Report on Patentability (Chapter I of the Patent Cooperation Treaty) for PCT/US2015/023136, Applicant: The Regents of the University of California, Form PCT/IB/326 and 373, dated Oct. 13, 2016 (13pages).

Liu, Kai et al., Improved-Throughput Traction Microscopy Based on Fluorescence Micropattern for Manual Microscopy, Plos One, www.plosone.org, Aug. 2013, vol. 8, Issue 8, e70122 (11pages).

Marinkovic, Aleksandar et al., Improved throughput traction microscopy reveals pivotal role for matrix stiffness in fibroblast contractility and TDF-B responsiveness, Am J Physiol Lung Cell Mol Physiol 303: L169-L180, 2012. First published Jun. 2012; doi:10.1152/ajplung.00108.2012.

Munevar, Steven et al., Traction Force Microscopy of Migrating Normal and H-ras Transformed 3T3 Fibroblasts, Biophysical Journal, vol. 80, Apr. 2001, 1744-1757.

Polio, Samuel R. et al., A micropatterning and image processing approach to simplify measurement of cellular traction forces, Acta Biomater. Jan. 2012; 8(1):82-88. doi:10.1016/j.actbio.2011.08.013.

Rape, Andrew D. et al., The regulation of traction force in relation to cell shape and focal adhesions, Biomaterials 32 (2011) 2043-2051.

Tseng, Peter et al., Substrates with Patterned Extracellular Matrix and Subcellular Stiffness Gradients Reveal Local Biomechanical Responses, Adv. Mater. 2014, 26, 1242-1247.

Wang, James H-C. et al., Cell traction force and measurement methods, Biomechan Model Mechanobiol (2007) 6:361-371.

* cited by examiner

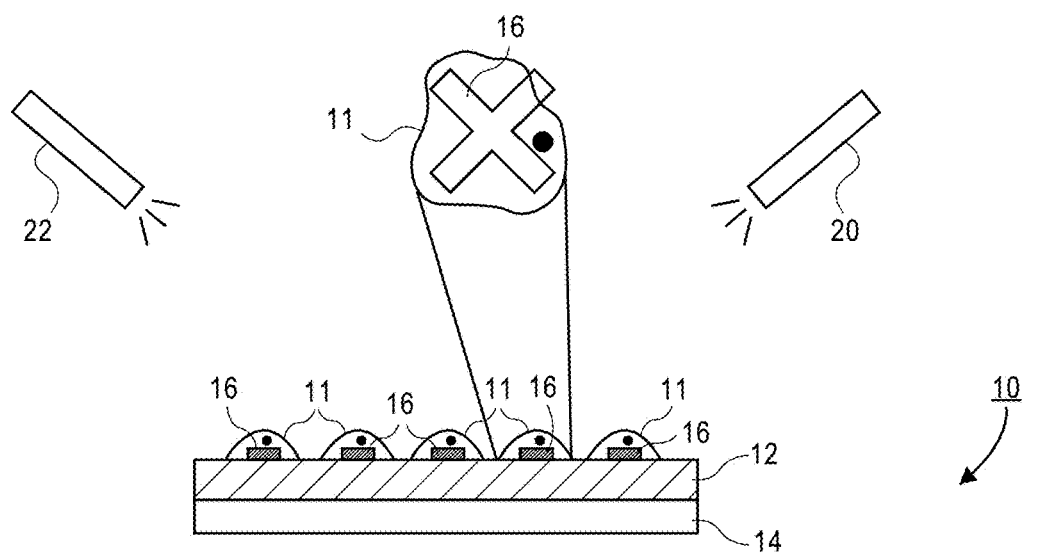
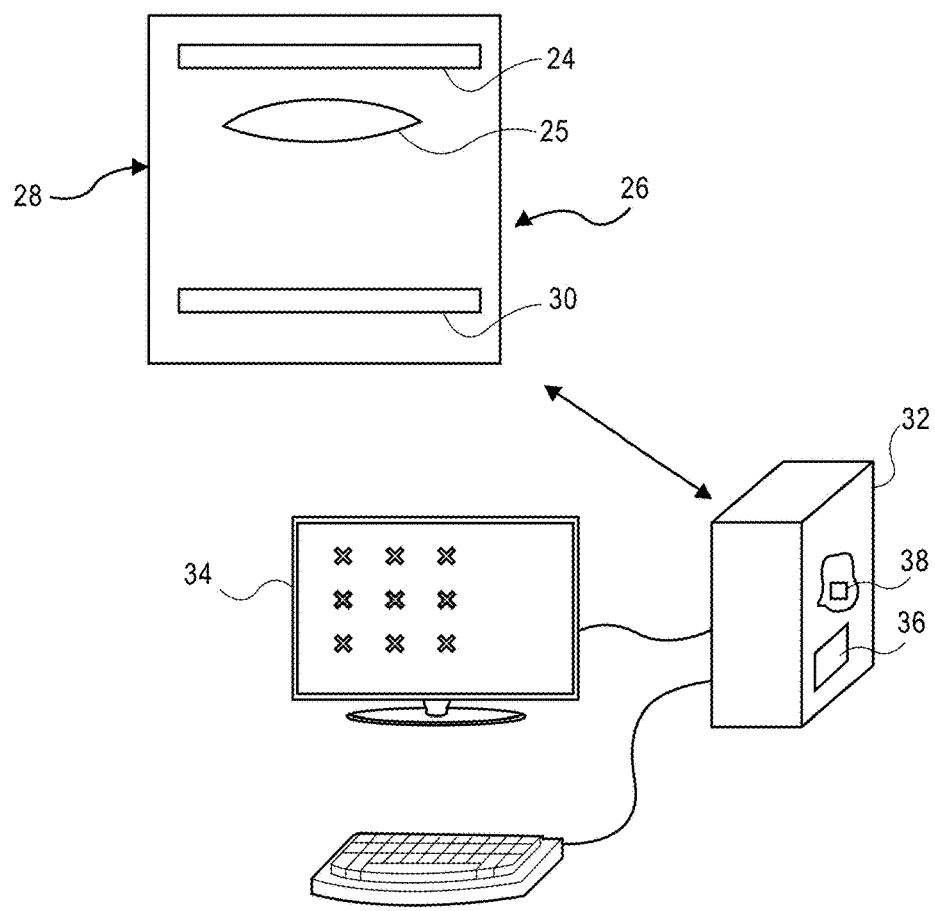
FIG. 1

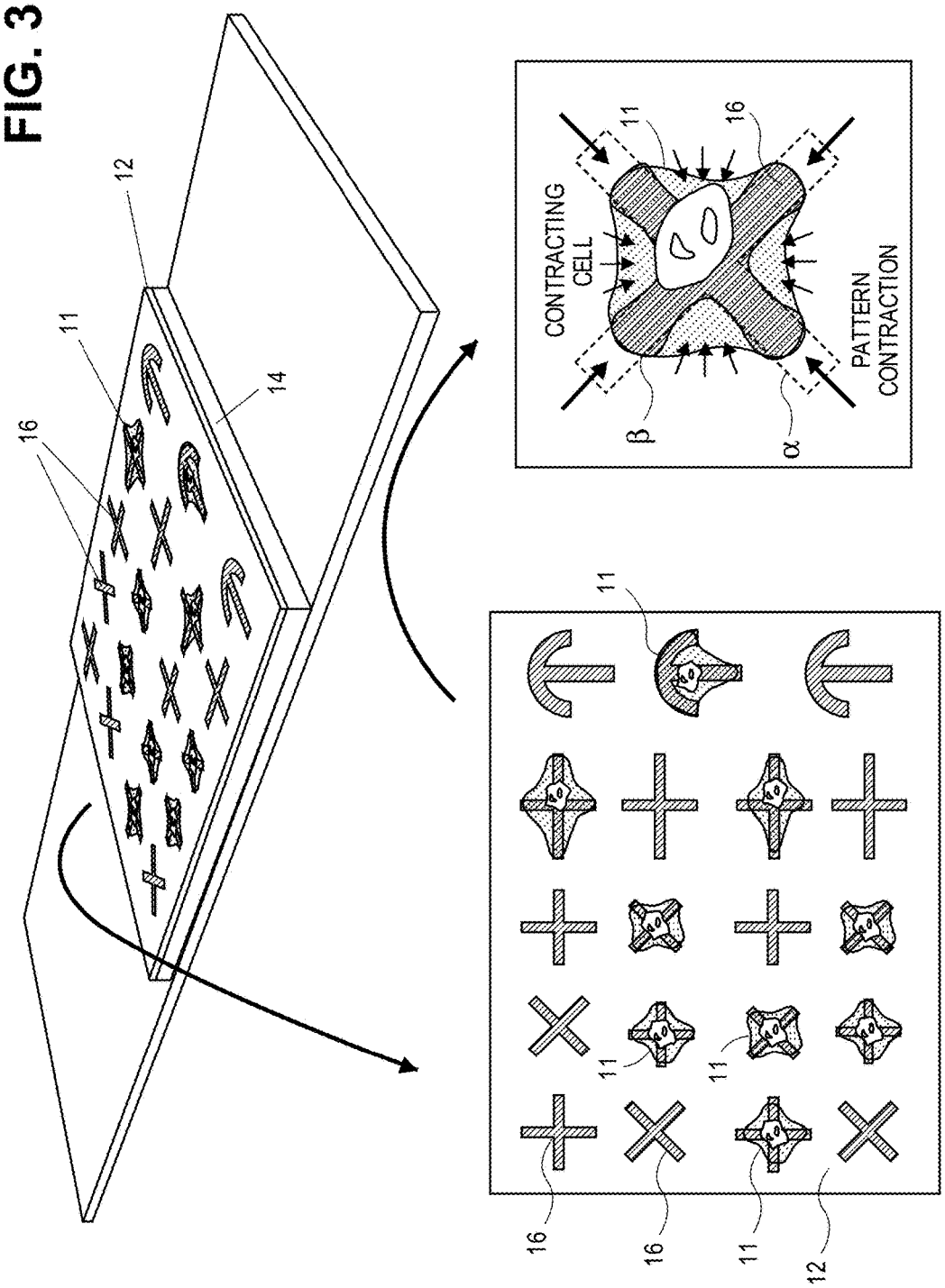

INPUT:
FLUORESCENT PATTERN
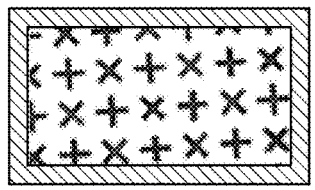
DAPI NUCLEAR STAIN
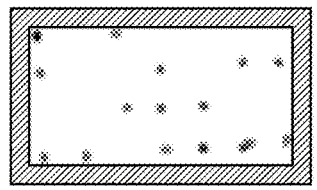
CROSS-REFERENCE
PROCESSING:
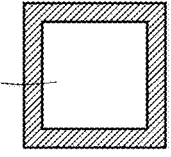
DAPI
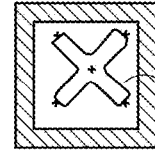
FITC
NO CELL
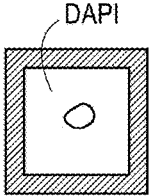
DAPI
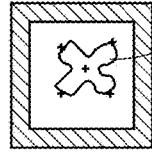
FITC
1 CELL
OUTPUT:
CONTROLS
DEFLECTION (MICRONS)
CASES
SIGNAL
DEFLECTION (MICRONS)
CASES
FIG. 8

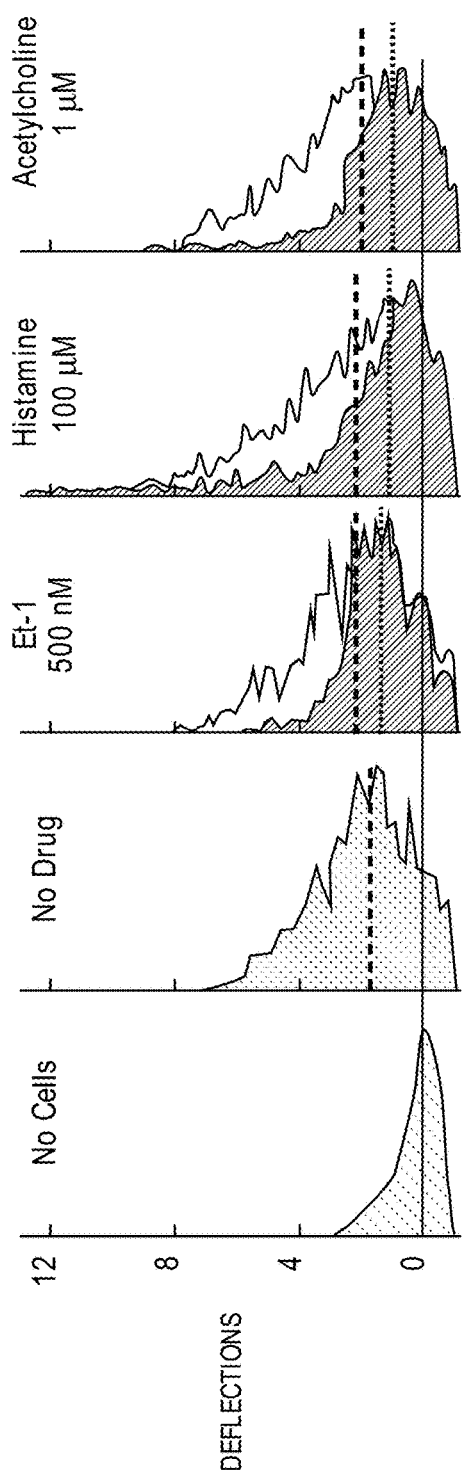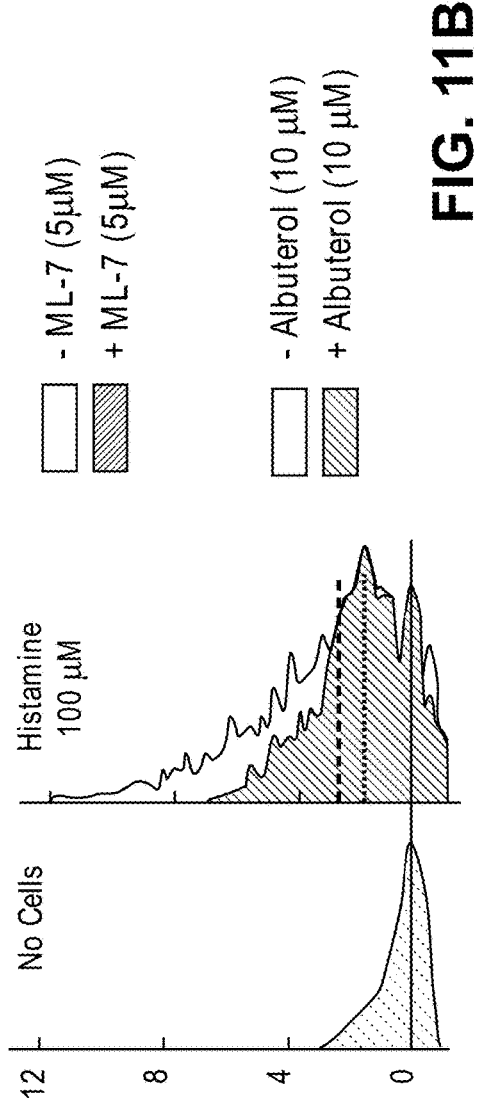
FIG. 11A
FIG. 11B

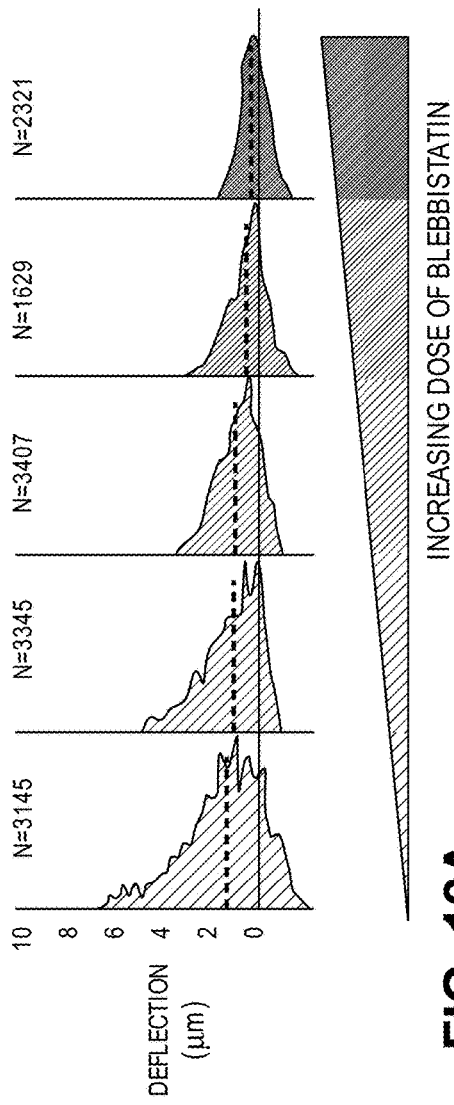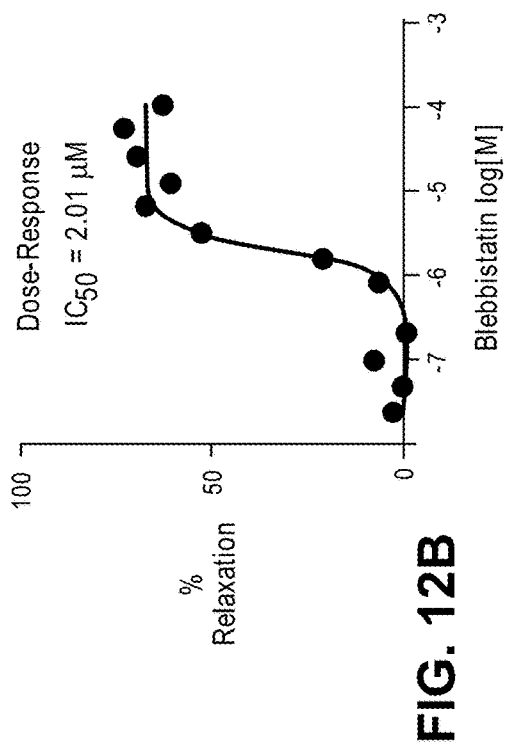
FIG. 12A
FIG. 12B

DEVICE AND METHOD FOR FORCE PHENOTYPING OF CELLS FOR HIGH-THROUGHPUT SCREENING AND ANALYSIS

RELATED APPLICATION

This Application is a continuation of U.S. application Ser. No. 15/300,021, filed on Sep. 28, 2016, now issued as U.S. Pat. No. 10,082,497, which is a U.S. National Stage filing under 35 U.S.C. § 371 of International Application No. PCT/US2015/023136, filed Mar. 27, 2015, which claims priority to U.S. Provisional Patent Application No. 61/972,171 filed on Mar. 28, 2014, which are hereby incorporated by reference. Priority is claimed pursuant to 35 U.S.C. §§ 119, 120 or any other applicable statute.

STATEMENT REGARDING FEDERALLY SPONSORED RESEARCH AND DEVELOPMENT

This invention was made with government support under Grant Number OD007113, awarded by the National Institutes of Health. The government has certain rights in the invention.

FIELD OF THE INVENTION

The technical field generally relates methods and devices used for determining and/or assaying forces applied by cells.

BACKGROUND

Current technologies used to study cell contractile forces include traction force microscopy (TFM) of substrates having embedded fluorescent particles. In TFM, cells are cultured as a monolayer on the surface of a thin substrate with fluorescent microspheres (e.g., latex beads) embedded therein. In another method, microfabricated silicone elastomeric post arrays have been developed for measuring the traction forces of adherent cells. See e.g., Sniadecki et al., Microfabricated Silicone Elastomeric Post Arrays for Measuring Traction Forces of Adherent Cells, Methods in Cell Biology, Vol. 83 (2007). In this method a vector map of traction forces is obtained by measuring the deflection of each micropost. Cellular contractile forces can also be measured indirectly by atomic force microscopy (AFM). AFM has been used to measure stiffness of cell cytoskeleton, which is broadly correlated to contractility through myosin contraction of the actin cytoskeleton. These approaches have been used to map stem cells, and correlated to the metastatic potential of cancer cells. Elastomeric micropillars have been used to track the contractility of stem cells, and researchers have found variation in contractility during differentiation. See J. Fu, et al., Mechanical regulation of cell function with geometrically modulated elastomeric substrates, Nature Methods, Vol. 7, pp. 733-739, (2010).

TFM, which operates by mapping forces on the substrate as cells translocate across soft substrates and stretch the substrate, has been used to map forces in the leading vs. retracting edge during cell migration. Despite the usefulness of these methodologies, these techniques are not amenable to simple, high-throughput extraction of contractility measures from mixed populations of cells with rare sub-populations that need high numbers to statistically sample. These types of samples would be seen from a patient sample or mixed culture. Additionally, these previous techniques require high-resolution imaging and precise focusing of optical systems which make them less compatible for high-throughput analysis needed for example in attempting to screen for effect of a large number of drugs on force production. There thus is a need for better methods and systems for identifying and quantifying the forces applied by cells, including populations of cells with rare phenotypes.

SUMMARY

In one aspect of the invention, a system for assaying forces applied by cells includes an optically transparent substrate comprising a soft material having a Young's modulus within the range of about 3 kPa to about 100 kPa. An array of molecular patterns is disposed on a surface of the optically transparent substrate, the molecular pattern comprising fluorophore-conjugated patterns adherent to cells. The system includes at least one light source configured to excite the fluorophore-conjugated patterns. For example a first light source may be an excitation light source for the fluorophore-conjugated patterns. The second light source may be used to excite or pump another fluorophore. For example, another different fluorophore may be used to detect an organelle within the cell (e.g., cell nucleus). The light sources may include light emitting diodes (LEDs), laser diodes, or the like. The system includes an imaging device that is configured to capture fluorescent light emitted from the fluorophore-conjugated patterns. The imaging device may also be used to capture fluorescent light emitted from fluorescently labelled organelles such as the cell nuclei. The cell nuclei can be used to identify those fluorophore-conjugated patterns in which no cells adhere, one (1) cell adheres, or two (2) or more cells adhere. According to some embodiments, the fluorophore-conjugated patterns where no cells adhere are used as a control. In addition, in some aspects of the invention, the fluorophore-conjugated patterns where two or more cells adhere are discarded. However, in some embodiments, useful information may be obtained from fluorophore-conjugated patterns where two or more cells have adhered. Furthermore, immunofluorescence or other techniques may be used to introduce yet another fluorophore-conjugated molecule emitting fluorescent light at a third wavelength for the purpose of labeling and identifying, for example, surface markers on the cells and relating those to the information obtained from the imaged fluorophore-conjugated patterns.

In another embodiment of the invention, a system for assaying forces applied by cells includes an optically transparent substrate comprising a soft material having a Young's modulus within the range of about 3 kPa to about 100 kPa. The system includes an array of molecular patterns disposed on a surface of the optically transparent substrate, the molecular pattern comprising fluorophore-conjugated patterns adherent to cells. A second substrate containing a plurality of apertures therein is secured to the surface of the optically transparent substrate to form a plurality of wells wherein each well contains one or more molecular patterns therein (e.g., a subset of patterns can be contained within each well). For example, the second substrate could include 96 wells as is used in a conventional 96 well test plate (of course other number of wells could be used). The system includes at least one light source configured to excite the fluorophore-conjugated patterns. The excited fluorophore-conjugated patterns emit fluorescent light that is captured by an imaging device. A computing device is configured to receive images from the imaging device and measures a dimensional change of the fluorophore-conjugated patterns having cells disposed thereon. The dimensional change may include a contraction of the pattern (i.e., pattern gets smaller in some respect) or it may include a relaxation (i.e., pattern gets larger in some respect), or a skewing (i.e., pattern gets smaller or larger in a non-uniform manner).

In another aspect of the invention, a method of using the system described above includes the operations of loading the plurality of wells with cells so that at least some of the cells adhere to the fluorophore-conjugated patterns. In one embodiment, the array of wells can be used to analyze compounds or drugs for their ability to affect changes in protein targets, signaling pathways, the cellular membrane or cytoskeletal structures that impart force on the underlying patterned substrate. For example, some of the wells or each well is loaded with a different compound or drug and the plurality of wells are illuminated with the at least one light source simultaneously or in a well-by-well sequence in time. The fluorophore-conjugated patterns from the plurality of wells are imaged with the imaging device and a dimensional change of the fluorophore-conjugated patterns within the wells is measured. Certain cells or sub-populations of cells can be identified by a dimensional change that exhibits a certain characteristic. For example, the computer may identify those cells having a dimensional change above or below a threshold value or a dimensional change within a specific range.

In another aspect of the invention, a method of identifying the force phenotype of cells includes providing an optically transparent substrate comprising a soft material having a Young's modulus within the range of about 3 kPa to about 100 kPa. The optically transparent substrate has an array of molecular patterns disposed on a surface thereof, the molecular pattern comprising fluorophore-conjugated patterns adherent to cells. Cells are loaded onto the optically transparent substrate, wherein at least some of the molecular patterns have one or more cells adhered thereto. The fluorophore-conjugated patterns are illuminated and images are captured of fluorescent light emitted from the fluorophore-conjugated patterns with an imaging device. A dimensional change of the fluorophore-conjugated patterns is measured with a computing device that receives the images. The cells are then categorized or classified based at least in part on the measured dimensional change.

In another aspect of the invention, a method of forming a substrate having an array of fluorescent-conjugated molecular patterns includes providing an optically transparent substrate. A layer of polydimethylsiloxane (PDMS) is formed on the optically transparent substrate having a Young's modulus within the range of about 3 kPa to about 100 kPa. Next, a photoresist is patterned on the layer of PDMS. Fluorescently-conjugated molecules are attached to the layer of PDMS patterned with the photoresist. The photoresist is then removed.

In another aspect of the invention, a method of forming a substrate having an array of fluorescent-conjugated molecular patterns includes preparing a polydimethylsiloxane (PDMS)-based stamp having a desired array of patterns. A plurality of fluorescently-conjugated molecules is attached to the array of patterns of the stamp. The stamp is pressed to transfer the molecular pattern onto a layer of dextran spun to achieve a thin layer on a flat substrate. A soft layer of PDMS is formed on the stamped dextran, where the PDMS layer has a Young's modulus within the range of about 3 kPa to about 100 kPa. The dextran layer is then sacrificed to release the soft layer of PDMS. The soft layer of PDMS is then mounted on an optically transparent substrate.

BRIEF DESCRIPTION OF THE DRAWINGS

FIG. 1 schematically illustrates one embodiment of a system for assaying and measuring forces applied by cells.

FIG. 3 illustrates a perspective view of an optically transparent substrate with a layer of soft polymer material disposed on the substrate and containing a plurality of fluorescent molecular patterns thereon. Also illustrated is a top view as well as a magnified view of a single pattern.

FIG. 8 illustrates how representative input images of the layer that is obtained with the imaging device are processed by the imaging processing software to generate deflection data.

FIG. 11A illustrates the contraction of airway smooth muscle (ASM) cells that were exposed to acetylcholine, enodthelin-1, and histamine. ML-7 was also added after contraction and was shown to relax smooth muscle contraction. This is seen by the reduction in deflection amount that was measured after addition of myosin light chain kinase inhibitor ML-7 (+ML-7). The negative control is also illustrated (−ML-7). Deflections on the y-axis are in micrometers.

FIG. 11B illustrates the contraction of ASM cells in response histamine as well as the resulting relation in response to the addition of albuterol (+ Albuterol).

FIG. 12A illustrates respective deflection graphs as function of increasing blebbistatin concentration for HeLa cells.

FIG. 12B illustrates a dose-response curve for blebbistatin concentration as a function of percentage relaxation for HeLa cells.

DETAILED DESCRIPTION OF THE ILLUSTRATED EMBODIMENTS

Figure 2A:
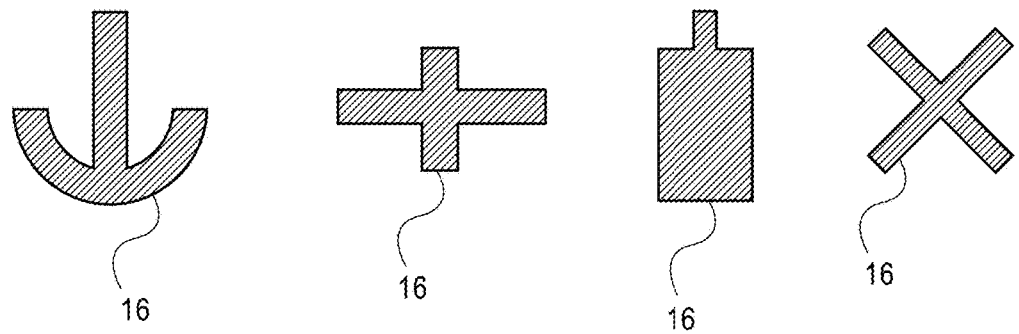
FIG. 2A illustrates illustrative shapes and configurations for fluorescent molecular patterns that are used as part of the system.

FIG. 1 schematically illustrates one embodiment of a system 10 for assaying forces applied by cells 11. In this embodiment, a layer 12 of soft polymer material is disposed atop an optically transparent, rigid substrate 14. The layer 12 of soft polymer material includes one or more molecular patterns 16 as described in more detail below. The molecular patterns 16 are formed within or applied directly onto the layer 12 of soft polymer material and are fluorophore-conjugated patterns 16 that are adherent to cells 11 that are placed onto the layer 12 of soft polymer material. The fluorophore-conjugated molecular patterns 16 are used to precisely control the locations and shapes of adhered cells 11, and for direct visualization of the forces the adhered cells 11 apply (or, conversely, don't apply) to the layer 12.

The layer 12 is soft enough such that the soft polymer material that forms the layer 12 can be deformed at least 1 μm by forces on the order of magnitude of those applied by cells 11, i.e., forces within the range of pN-nN. The height of this layer 12 of soft polymer material may vary but is generally less then around 20 μm in height. In one embodiment, the layer 12 of soft polymer material includes polydimethylsiloxane (PDMS). More particularly, the layer 12 of PDMS has a Young's modulus within the range of about 3 kPa to about 100 kPa and more preferably within the range of about 3 kPa to about 20 kPa. The softness of the PDMS layer 12 may be tuned by using a high base to crosslinker ratio (e.g., within a range of around 70:1 to around 20:1).

As seen in FIG. 1, the layer 12 of soft polymer material is secured to one surface of an optically transparent substrate 14. The optically transparent substrate 14 may include a glass material (e.g., glass slide, coverslip, or the like). In one aspect of the invention, low elasticity PDMS is spun onto the optically transparent substrate 14 to produce the layer 12. The adhesion between the PDMS layer 12 and the optically transparent substrate can be enhanced through modifications to the surface of the optically transparent substrate 14 prior to spinning. For example, for an optically transparent substrate 14 formed from glass, plasma treatment followed by silanization prior to spin coating can be used. Alternatively, as explained below with respect to the process of FIG. 9, the PDMS layer 12 may be spun onto a dextran-coated flat substrate if the pattern transfer method is employed for creating the molecular patterns.

Still referring to FIG. 1, the PDMS layer 12 includes a plurality of fluorescently-conjugated molecular patterns 16. In one aspect, the fluorescently-conjugated molecular patterns 16 are formed as part of an array. The fluorescently-conjugated molecular patterns 16 are applied directly onto the surface of the PDMS layer 12. In one embodiment, the molecular pattern 16 may be a single labeled protein such as human IgG-FITC or it may be a combination or mixture of any number of proteins, of which one must serve as a reporter protein and be fluorescently labeled while the others engage the cells 11 and promote specific behaviors (e.g., fibrinogen-FITC as a reporter and unlabeled fibronectin to promote adhesion). The molecular pattern 16 can be of any shape and can either be symmetric or asymmetric. Preferably, molecular pattern 16 has a minimal line-width of about 3 microns. The molecular pattern 16 may have a number of shapes or configurations including, but not limited to, symmetric and asymmetric crosses, squares, circles (filled or un-filled), ellipses, ovals, rings, teardrop-like shapes, and others. FIG. 2A illustrates several different shapes that can be used for the molecular patterns 16. Shapes that are asymmetric can provide information on asymmetric forces that cells 11 apply. The various pattern shapes can be manipulated (e.g., sheared, enlarged, etc.) to allow for additional features of cell contractility to be measured. Since the molecular patterns 16 are within an order of magnitude of the size of cells 11, over 100,000 molecular patterns 16 can fit on a single substrate the size of a glass coverslip.

Figure 2B:
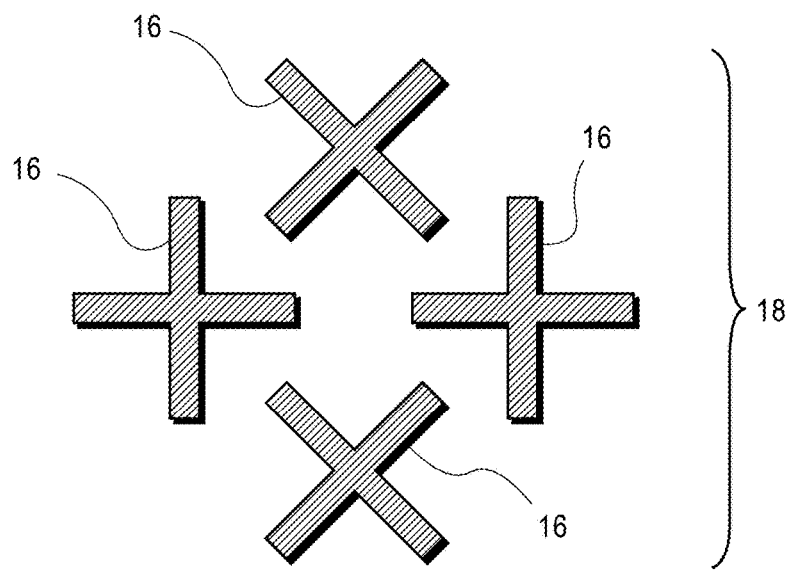
FIG. 2B illustrates an example of a unit cell containing multiple fluorescent molecular patterns arranged to increase cell density while minimizing cell-to-cell coupling.

FIG. 2B illustrates one configuration of molecular patterns 16 that are arranged in a unit cell 18 configuration to improve the information density of the molecular patterns 16. If portions of molecular patterns 16 are too close to one another, mechanical coupling of adjacent cells 11 can occur which will modify the apparent stiffness and can potentially lead to oscillations in contractions. The unit cell 18 configuration of FIG. 2B places regions of high traction away from each other such that higher densities of cells 11 can be achieved without cross-talk. Note that the unit cell 18 configuration may be repeated.

Referring back to FIG. 1, the system 10 further includes a first light source 20 which may include wavelength filtered arc lamp, a light emitting diode (LED) or laser diode or multiple LEDs or laser diodes. The first light source 20 emits light at a wavelength or wavelength range that excites the fluorophore that is part of the fluorophore-conjugated molecular patterns 16. In one optional aspect, the first light source 20 may be a tunable light source 20 in which different wavelengths can be selected. In such an embodiment, a single light source may be used instead of multiple light sources. In one preferred embodiment of the invention, the system 10 includes a second light source 22 that emits light at a different wavelength from the first light source 20. The second light source 22 may be used to excite another different fluorophore than the fluorophore-conjugated molecular patterns 16. In one aspect, the first and second light sources 20, 22 may be integrated into another device such as a fluorescent microscope 28. For example, as explained herein, the nucleus of the cell 11 may be stained with a fluorescent dye or other fluorescent reporter that emits light in response to excitation by the second light source 22. The light that is emitted from the nucleus of the cell 11 can be used to identify and count the number of cells 11 that have adhered to the molecular patterns 16. For example, imaging of the array of molecular patterns 16 may indicate the presence of two (2) cell nuclei disposed above a single molecular pattern 16 which is indicative that there are two cells 11 located on the single molecular pattern 16. Likewise, the absence of any stained nuclei above a molecular pattern 16 reflects that zero (0) cells 11 are located on that particular location of the molecular pattern 16. Additional wavelength excitation sources and emission filters may be used to characterize other molecular properties of adhered cells (e.g., immunofluorescence of cell surface proteins indicative of a specific cell type or state with fluorescently labeled antibodies) in combination with applied force and nuclear presence.

Stained cell nuclei may be counted by using two gates: (1) size, and (2) solidity. Larger sized objects must have high solidity to be considered a single nucleus. Smaller objects can have lower solidity (subject to a minimum threshold) and still be considered as having a single nucleus present. If the conditions are not satisfied, the object is rejected as having 2+ nuclei. The MATLAB software program and the functions "im2bw," "bwareaopen," "bwlabel," and "regionprops" can be used to determine the size and solidity of objects as well as perform the necessary binary image operations. Initially, the image containing DAPI (or other nuclear stain) is turned into a binary image and small objects are removed. Next, the number of distinct objects is determined in the binary image. If there are 0 or 2+ objects, these are classified as such and the next pattern location is chosen. If there is what appears to be a single object, the area (A) and the solidity (S) are calculated. The Solidity (S) is defined as the fraction of area of the object to the area of the smallest convex polygon (P) encompassing the object (S=A/P). The appropriate threshold for the area (A) is established based on the cell type. Smaller objects are likely to be a single nucleus and will have a lower threshold for an acceptable S value while larger objects are more likely to be two or more overlapping nuclei and therefore will have a higher minimum S value to be deemed a single nucleus. After establishing the threshold cutoff for the S value, the measured S value is compared to the threshold value. If the measured S value is higher than the threshold or cutoff value then the object is considered a single nucleus. If the measured S value is below the threshold value it is considered 2+ nuclei.

Still referring to FIG. 1, an optional filter 24 is provided in the optical path that formed between the layer 12 and an imaging device 26. The optional filter 24 is used to filter out excitation light from the light source(s) 20, 22 while permitting the passage of fluorescent light that is emitted from the fluorescent dye or probes. The light sources 20, 22 may also be oriented obliquely with respect to the layer 12 which can assist with rejection/filtering of the excitation light. The optional filter 24 may be secured to the optically transparent substrate 14 or it may even be removable within the optical path as opposed to being located within the imaging device 26. Still referring to FIG. 1, the system 10 includes an imaging device 26 that is positioned along the optical path so as to acquire images of the fluorophore-conjugated molecular patterns 16 including optional images of stained features or organelles within the cells 11. The imaging device 26 may include optical components of an inverted fluorescent microscope 28. The optical components include, for example lenses 25 that are used to magnify the image of the layer 12 containing the fluorescent molecular patterns 16. Typical magnification used for the fluorescent magnification is 10× which allows more rapid imaging of a large number of cells to obtain statistically relevant data in a shorter time than in previous techniques to measure cell forces. The fluorescent microscope 28 includes a CCD or CMOS imaging sensor 30 that is used to capture two dimensional digital image frames. The imaging device 26 is able to capture two dimensional image frames which contain fluorescent images of the fluorophore-conjugated molecular patterns 16. The fluorescent microscope 28 may include filters 24 therein. For example, cells 11 can be imaged with UV and blue excitation channels corresponding with blue and green emission filters, respectively. The fluorescent microscope 28 may include "green" (e.g., 488 nm) or "red" (e.g., 532 nm) channels that are used for imaging the fluorescent pattern 16. A "blue" channel (e.g., about 360 nm) may be used to image DAPI or Hoechst stains that are used to label cell nuclei.

As noted herein, the fluorophore-conjugated molecular patterns 16 may be patterned in an array on the layer 12. In particular, the location of each fluorophore-conjugated molecular pattern 16 can be identified so that contractile motion of any particular molecular pattern 16 can be associated with a particular cell 11 or cells 11 that may be adhered to that spot. In this regard, one or more landmarks may be provided on the layer 12 or optically transparent substrate 14 so that specific locations can be mapped. In one example, the molecular patterns 16 may be arrayed in rows and columns. For example, unit cells 18 may be arrayed in rows and columns in the layer 12. In one example that is described below in more detail, the molecular patterns 16 are contained within individual wells or chambers so that separate reaction areas are provided. These segregated wells or chambers can be used to test compounds or pharmaceutical compositions on cells 11 to investigate their ability to affect contractile movements or force generation, for example.

Still referring to FIG. 1, the system 10 includes a computing device 32 that is operably coupled to the imaging device 26. The computing device 32 may include a computer which may be a personal computer, laptop, tablet, or the like. The computing device 32 is associated with a display 34 that can be used to display images of the molecular patterns 16 in the layer 12 along with other fluorescent images of organelles or the like that are stained or otherwise emit fluorescent light. Data that is generated by the imaging processing software 36 executed by the computing device 32 may also be presented on the display 34. Data can include, for example, dimensional changes of the molecular patterns 16, rates of change of the dimensional change in the molecular patterns 16. Data can also include histogram or binned data pertaining to cells 11 that are adhered to the molecular patterns 16. For example, cells 11 that have dimensional changes exceeding a particular threshold amount or range can be identified. The computing device 32 includes at least one processor 38 that is used to execute image processing software 36 as described below.

A description will be given of how the image processing software 36 processes the digital image frames obtained by the imaging device 26. Image frames may be saved with the .TIFF format to preserve information for analysis or later viewing. The image frames may also optionally be saved in the compressed .PNG format. Of course, any valid image format (e.g., .jpg, .bmp, or the like can be used). After cells have been placed or otherwise incubated with the layer 12 and allowed to adhere to the molecular patterns 16, the array of patterns 16 is then imaged with the imaging device 26. The imaging device 26 may obtain fluorescent images of the molecular patterns 16 before, during, or after the cells 11 have undergone contractile movement or, conversely, relaxation. The dynamic range of the pixel intensities may be adjusted post-imaging using, for example, ImageJ so that the patterns 16 can be visualized.

Figure 10:
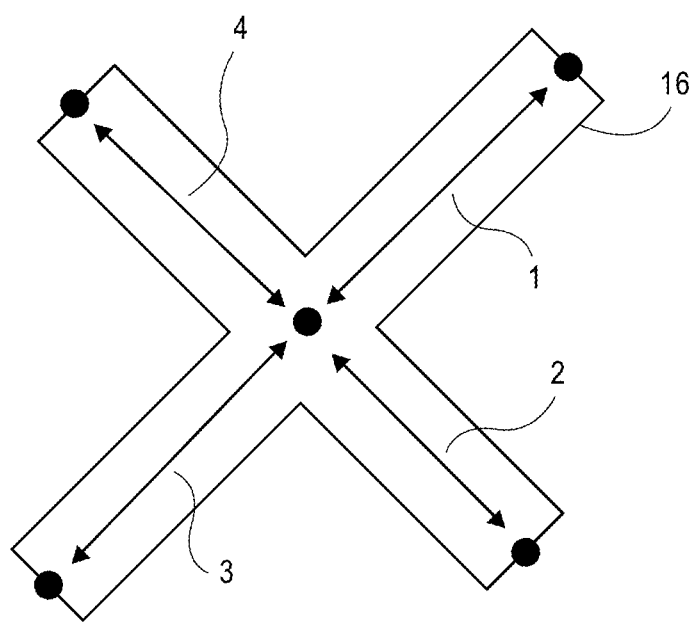
FIG. 10 illustrates a single pattern showing the identified center of the pattern along with the four (4) measurements for each "arm" of the pattern.

The image processing software 36 identifies all instances of a given molecular pattern 16 in an image stack and determines how many cells (e.g., 0, 1, or 2+) are adhered to each pattern 16 based on images of those cells 11 with stained nuclei. A MATLAB script opens the image files and pairs the stained nuclei images (e.g., DAPI images) with the fluorescent images of the patterns 16 (e.g., FITC images). The image processing software 36 calculates characteristic pixel length(s) of a given pattern 16 for the cases of no cells adhered and one (1) cell adhered. The 'FITC' images may be linearly scaled up with, for example, the MATLAB function 'imresize' to improve resolution of these measurements. For those patterns with zero cells adhered thereto, the center of each pattern 16 may be determined using binary center-of-mass calculations. For those patterns 16 with one (1) cell adhered thereto, a series of binary dilation and erosion operations, followed by a binary center-of-mass calculation on patterns is performed. The erosion/dilation procedure is used to remove the potential asymmetry in the pattern 16 arising from cell-induced deformations that would otherwise impact the location of the center of mass. Patterns 16 with two or more nuclei are not analyzed. For each processed pattern 16 (those that are crosses or "X" shaped), the diagonal distance in pixels is measured between the calculated center and the bright edge of the pattern 16 in each direction as illustrated in FIG. 10. This results in four (4) measurements per pattern 16. These measurements are stored, converted to microns based on the magnification used (typically 10×). These lengths are normalized to the median of those measured in patterns 16 with no cells (nominally 0 pixel deformations which is used as a control) and a relative distribution plot for patterns with one (1) cell is generated (see FIG. 8). Cropped images of each pattern 16 screened by the image processing software 36 in a given location and the images of the corresponding cell nuclei on those patterns 16 are saved and may be reviewed if an execution error is suspected. FIG. 8 illustrates examples of cropped DAPI and FITC images.

If a circular shaped pattern 16 is used, the MATLAB "imfindcircles" function can be used to locate circles falling within a certain radius range, and the center (x,y) and the radius (r, in pixels) for each circle can be stored. The same nuclei counting function as described above is used to determine the number of cells 11 on each pattern 16. The radii in pixels are converted to microns, and the differences between each of the radii of circle-patterns with 1 cell and the median of the radii of circle-patterns with 0 cells can then be plotted as a distribution as described above with respect to the non-circular pattern 16.

The image processing software 36 can take absolute measurements of patterns 16 if the dynamic analysis is used. Thus, the imaging processing software 36 is able to calculate dimensional changes of the molecular patterns 16 occurring in response to cytoskeletal changes in the cells 11. The dimensional changes can be monitored in real time for dynamic monitoring of cell-substrate interaction or dimensional changes can be measured using end-point analysis where forces applied on the layer 12 reach a steady-state.

FIG. 3 illustrates a perspective view of the layer 12 of soft polymer disposed atop an optically transparent substrate 14 along with a top view of the layer 12. A magnified view of a single pattern 16 containing a single cell 11 is also illustrated in FIG. 3. Different molecular patterns 16 are illustrated formed in an array on the layer 12. Cells 11 are illustrated as being adhered to some of the fluorescently adhesive molecular patterns 16. FIG. 3 also illustrates a magnified view of a single cell 11 (with nucleus) adhered to one of the molecular patterns 16. In this example, the molecular pattern 16 is in the shape of an "X" that has contracted in response to the contracting cell 11. The original shape of the "X" pattern 16 is illustrated in outline a as well as the contracted shape β.

Figure 4A:
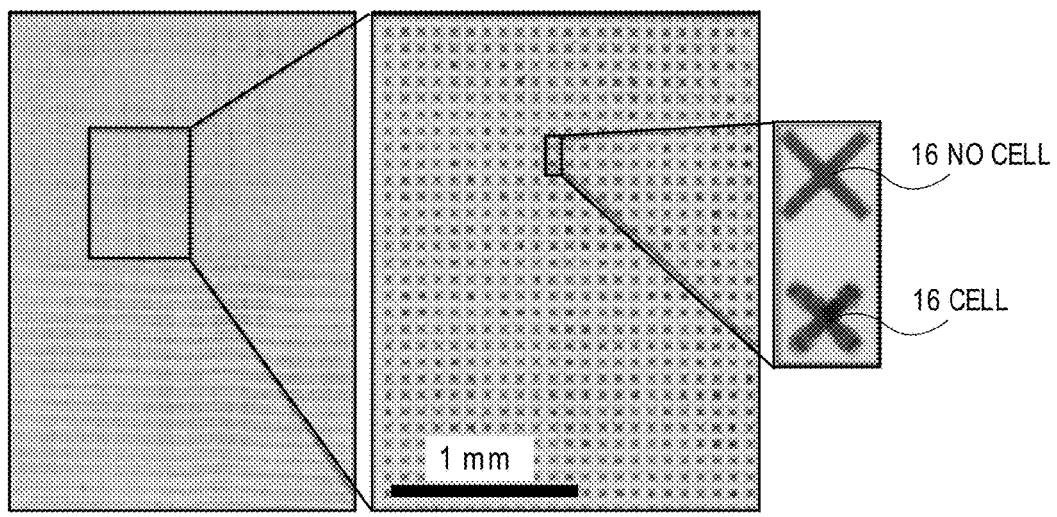
FIG. 4A illustrates a fluorescent image taken of an array of molecular patterns disposed on a layer. Successively magnified images are illustrated with the final image showing two (2) such patterns. One pattern (upper) has no cells adhered thereto. The other pattern (lower) has contracted inward in response to forces exerted on the layer by the cell.
Figure 4B:
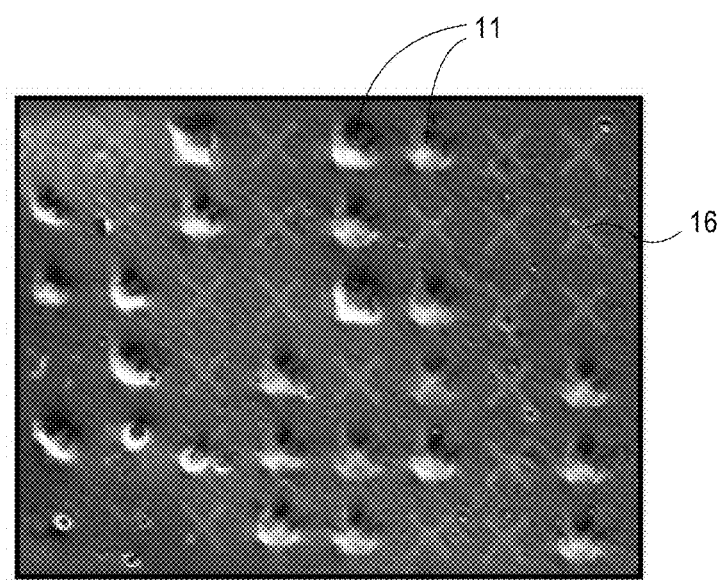
FIG. 4B illustrates a brightfield image of a portion of the layer containing the fluorescent pattern. Cells are seen on some of the molecular patterns.
Figure 5:
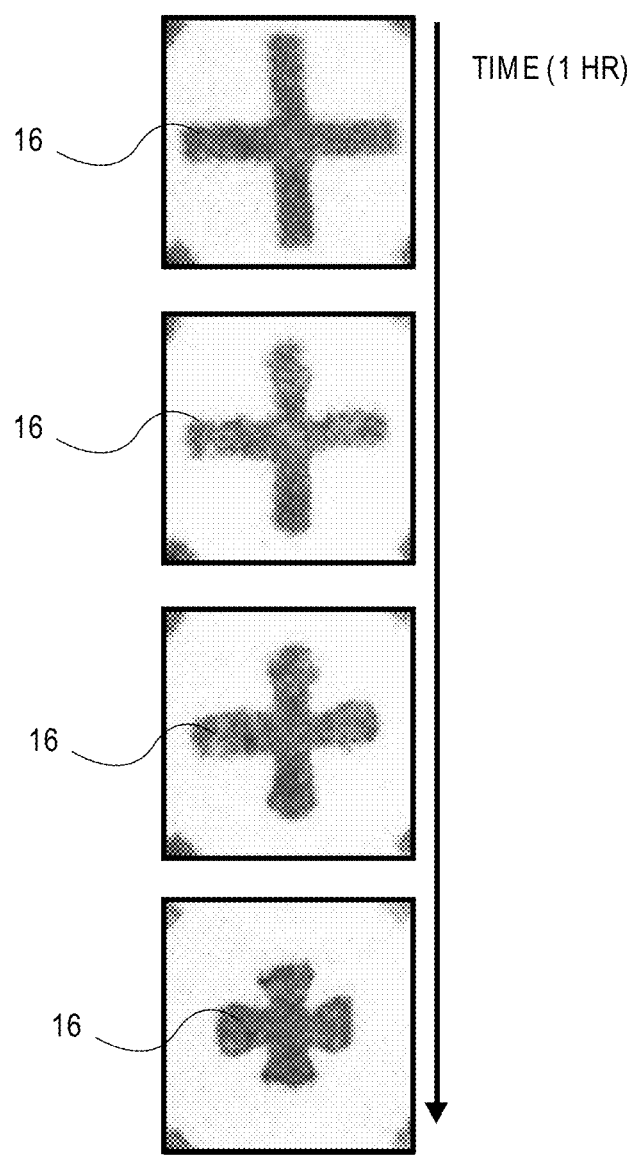
FIG. 5 illustrates still images from a time lapse video of a vascular smooth muscle cell contracting a green fluorescent fibrinogen and non-fluorescent fibronectin pattern. As time progresses, one can see now the cross-shaped pattern compresses in both directions (perpendicular axes) but does not peel from the substrate.

FIG. 4A illustrates a fluorescent image taken of an array of molecular patterns 16 disposed on a layer 12. Successively magnified images are illustrated with the final image showing two (2) such patterns. One pattern 16 (upper) has no cells 11 adhered thereto and so the pattern 16 retains its original shape. The other pattern 16 (lower) has contracted inward in response to forces exerted on the layer 12 by the cell 11. FIG. 4B illustrates a brightfield image of a portion of the layer 12 containing the fluorescent pattern 16. Cells 11 are seen on some of the molecular patterns 12. FIG. 5 illustrates a time lapse video still images of vascular smooth muscle cell contracting a green fluorescent fibronectin pattern 16. As time progresses, one can see now the cross-shaped pattern 16 compresses in both directions (perpendicular axes).

Figure 6A:
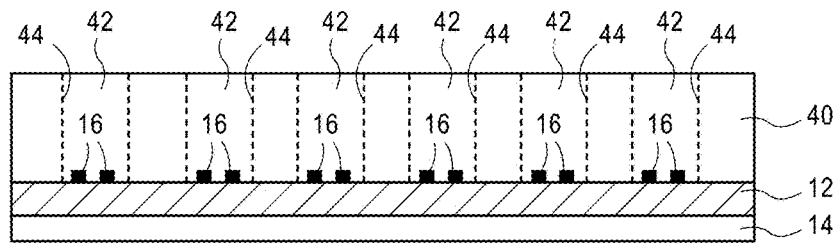
FIG. 6A schematically illustrates another embodiment of a system for assaying and measuring forces applied by cells. This embodiment uses a plurality of wells. A side view of the well-based device is illustrated.
Figure 6B:
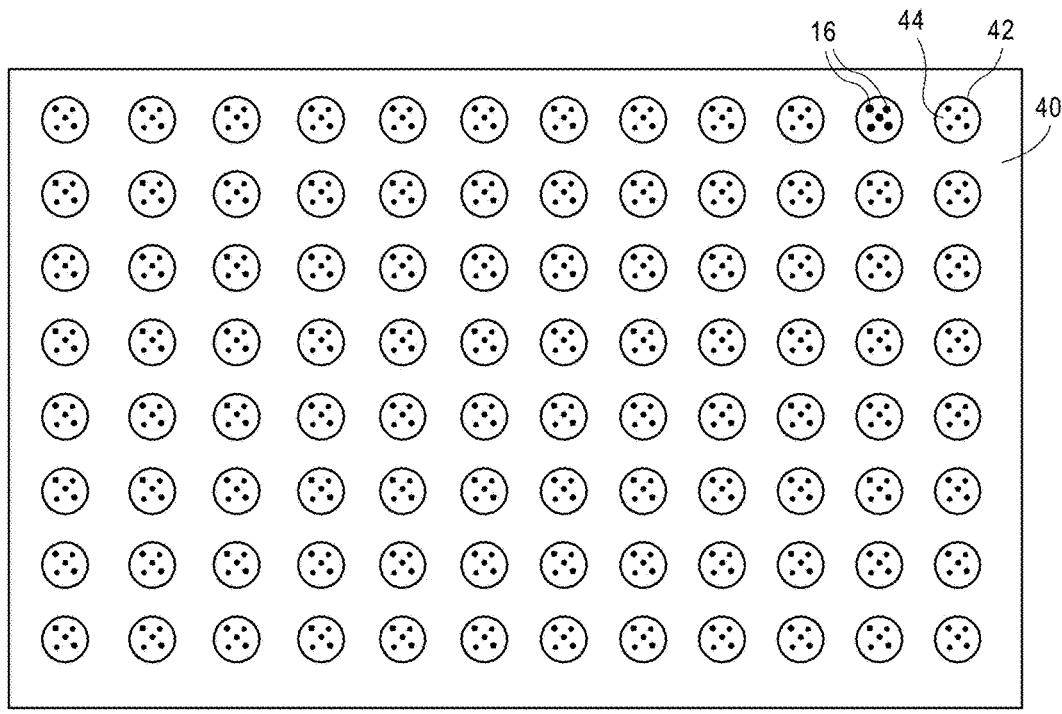
FIG. 6B illustrates a top view of the device of FIG. 6A. 96 wells are illustrated although more or less can be used (e.g., 384).

FIGS. 6A and 6B illustrate another embodiment of the invention. In this embodiment, a substrate 40 such as a plate having apertures 42 formed therein (non-tapered) is adhered to the layer 12 such that individual wells 44 are formed over the surface of the layer 12 with each well 44 containing a plurality of fluorescent patterns 16. For example, each well 44 may circumscribe a region of the layer 12 such that large numbers of fluorescent patterns 16 are formed therein (e.g., between 10,000 and 100,000). Advantageously, each well 44 contains the same number of patterns 16 with the same pattern shapes. In this regard, each well 44 contains a similar reaction environment. This embodiment may be useful for drug discovery applications. For example, a different compound or drug of interest or cocktail thereof can be loaded into different wells 44 which can then be individually examined for the respective force response(s) of the adhered cells 11. Not only is this embodiment useful for screening but it can also be used with different concentrations of the same compound or drug of interest to determine dose-response effects on contractility or cell viability.

The substrate 40 is adhered to the layer 12 and surface tension from the wetting solution ensures a quick and effective bond between the substrate and the layer 12. A roller applicator or the like may be used to apply uniform pressure to the substrate 40 and/or optically transparent substrate 14 holding the layer 12. This results in a water-tight seal. In an alternative embodiment, an adhesive or clamp (not shown) may be used to secure the substrate 40 to the layer 12. In this embodiment, the wells 44 are filled with solution to keep the layer 12 wet. Once cells 11 are ready to be seeded onto the patterns 16 within the wells 44, the wells 44 can be filled with media and incubated until the cell suspension is prepared and loaded into the wells 44.

Figure 7:
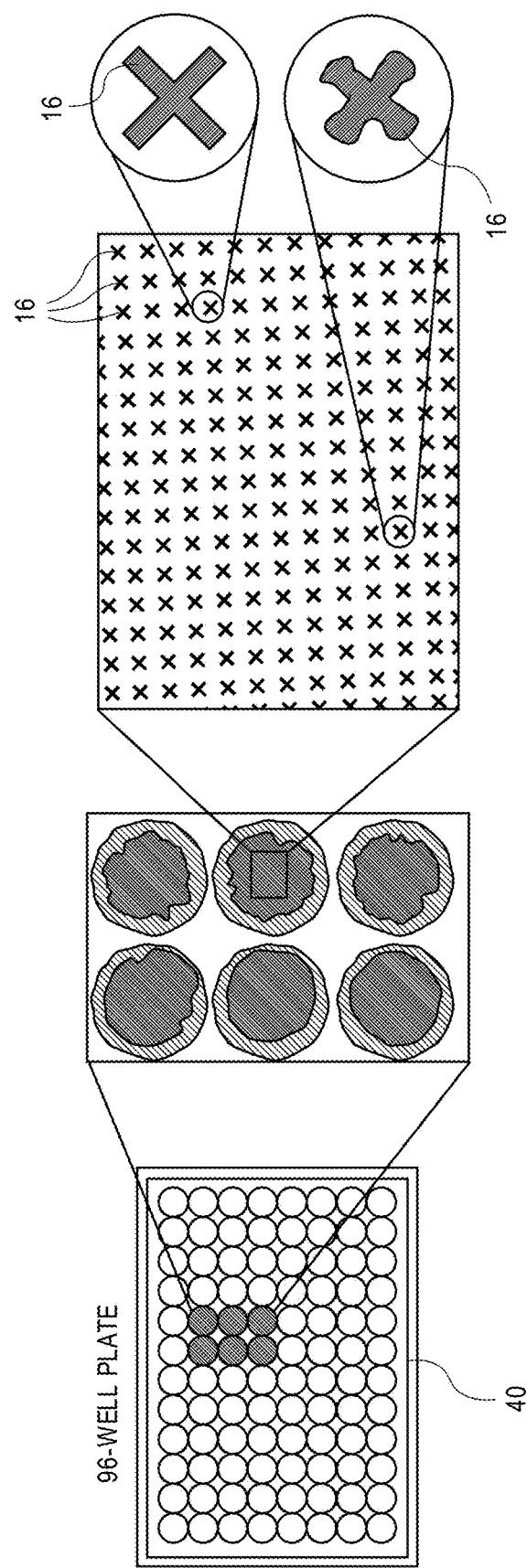
FIG. 7 illustrates successively magnified images of an embodiment of the type illustrated in FIGS. 6A and 6B.

FIG. 7 illustrates successively magnified images of an embodiment of the type illustrated in FIG. 6. A 96 well substrate or plate 40 is illustrated. Six of the wells 44 are illustrated in a magnified view followed by another magnified portion of the layer 12 within a single well 44. Finally, two different fluorescent patterns 16 are magnified and illustrated. The upper fluorescent pattern 16 contains no cells and illustrates a non-contracted pattern 16. Conversely, the lower fluorescent pattern 16 illustrates significant contraction of the arms of the "X" shaped pattern 16.

Referring now to FIG. 8 a description of how the image processing software 36 processes the images will now be described. FIG. 8 illustrates how representative input images of the layer 12 that is obtained with the imaging device 26 are processed by the imaging processing software 36 to generate deflection data. Specifically, FIG. 8 shows an image of the fluorescent patterns 16 and also illustrates an image of the same field of view with DAPI (4′,6-diamidino-2-phenylindole) stain. DAPI is a fluorescent stain that binds strongly to A-T rich regions in DNA. Each of these patterns 16 is identified and measured automatically with the image processing software 36. The image processing software 36 detects the center or centroid of each pattern 16 and denotes the location thereof (e.g., pixel location in image frame). The image processing software 36 also finds the terminal ends of the same pattern 16 which in this case includes an "X" shape and stores the respective locations (again pixel locations). The image processing software 36 identifies those "X" shapes within the pattern 16 where no cells 11 have adhered. This is done by using the DAPI channel of the fluorescent microscope 28 to image fluorescently labeled cell nuclei and obtain the DAPI image. Alternatively, a live cell cytoplasmic stain such as calcein AM or Celltracker™ (Life Technologies, Inc.) series of dyes can be used as long as the fluorescent emission does not significantly overlap with the adhesive pattern fluorescent emission. FIG. 8 illustrates a corresponding DAPI image of the same field of view of FIG. 8. The presence of the "dots" in the DAPI image indicates the presence of a cell 11 on the pattern 16 due to the stained nucleus. The image of the pattern 16 may have a number of data points associated with each pattern 16. For example, in the case of crosses or "X" shapes, a change may be defined by the change in distance from the cross or "X" center to the furthest points of each arm, totaling four (4) data points per pattern 16.

The image processing software 36 cross-references the image of the fluorescent pattern 16 with that obtained of the same field of view with the DAPI image and identifies those patterns 16 that do not have any cells 11 adhered thereto by identifying the patterns 16 that do not have any fluorescent nuclei. These patterns 16 are then used as the controls. For example, similarly shaped patterns with no cells 11 thereon may have their respective dimensions measured and a baseline established that is representative of no deflection in the pattern 16. The imaging processing software 36 uses the DAPI channel (or other non-overlapping channels for other cytoplasmic dyes) to identify those patterns 16 with only a single cell 11 or multiple cells 11. In one preferred aspect of the invention, the patterns 16 with only a single cell 11 are used to measure contraction or relaxation of the layer 12 in response to corresponding cellular force application changes. These images are cropped and saved for each identified pattern 16 and stored in a directory for access in case of an execution error is suspected as well as for confirming potential sub-populations and/or outlier data. Images with two or more cells 11 are discarded but in some embodiments, these images may be used. Changes in the dimension of the patterns 16 holding a single cell 11 is calculated by measuring the terminal ends of each these patterns 16 and subtracting a mean or average made of these same patterns 16 with no cells adhered thereto. In some embodiments, each pattern 16 may be associated with multiple data points (e.g., crosses or X shapes may have four (4) data points). Alternatively, different data points from a single shape may be combined into an average or mean dimensional change.

FIG. 8 illustrates respective DAPI and FITC images of single pattern 16 with no cells adhered thereto. FIG. 8 also shows respective DAPI and FITC images of the same pattern 16 with a single cell adhered thereto. As seen in the FITC image of the pattern 16 with one cell 11, the terminal ends of the pattern 16 have contracted inward due to the contractile forces placed on the layer 12 by the adhered cell 11. FIG. 8 illustrates the measured deflection in microns of both the control pattern locations (with no cell) and pattern locations with only a single cell. All gathered measurements are normalized to the median of the control data which is set to zero. The control locations are centered around zero (0) deflections with about +/− microns in deflection. Contrast this with the much wider deflection range demonstrated by those pattern locations that have a single cell.

The image processing software 36 can be used to measure dimensional changes along multiple different axes depending on the nature of the molecular pattern 16. For example, the pattern 16 may have a major and a minor axis that may be orthogonal to one another. In another embodiment, the pattern 16 may be circular shaped and the image processing software 36 may be used to fit the pattern 16 with a circle that can be used to measure the diameter or radius of portions of the pattern 16. In some instances, only a single dimension or axis is measured. In other embodiments, multiple axes are measured to determine contractility. Contractility in one dimension may be different from contractility in another dimension.

The image processing software 36 may run for end-point analysis of forces applied by cells 11 in steady-state and for dynamic monitoring of cell-substrate interaction. For end-point analysis, cells 11 of interest are seeded and cultured on the layer 12 for the needed period of time (~6 hrs. for cells that interact with the patterns solely through focal adhesions or <1 hr. for phagocytic cells). To end the experiment, the cells 11 may be fixed with 4% paraformaldehyde, stained with DAPI, and the substrate is mounted onto a glass slide for ease of handling, and imaged at any time. For dynamic analysis, the layer 12 is securely mounted to the imaging device 26. After the desired field-of-view is selected, cells 11 are seeded on the layer 12 and time-lapse imaging is used to record the dynamics of the cell-substrate interaction. This modality is well suited for measuring individual cellular responses to exposures to drugs or gene modifications, contractility dynamics and force profiles for cardiac myocytes or other beating cells, and for other measurements of rates of force application where it may be useful in uncovering dynamics that are masked in end-point analysis data. Certain cell types, such as some phagocytic cells, however, are imaged "live" even for end-point analysis as it has been found that paraformaldehyde treatment induces relaxation in certain cell types.

As an alternative to the imaging device 26 described above, imaging and analysis may also be done using a wide-field smart-phone or tablet PC based fluorescence and/or dark-field based microscopic imaging devices. See e.g., Wei, Q. et al. Fluorescent Imaging of Single Nanoparticles and Viruses on a Smart Phone. ACS Nano 7, 9147-9155 (2013) or H. Zhu, et al., "Cost-effective and Compact Wide-field Fluorescent Imaging on a Cell-phone", Lab on a Chip (2010) to enable use of the invention in the field, in resource poor settings, or simply at a lower cost. Fluorophore excitation can be achieved using light-emitting-diodes and/or laser diodes that are placed at an oblique angle with respect to the optical axis of the imaging design, which can assist with the rejection/filtering of the excitation beam. In this alternative embodiment, the fluorescent microscope 28 is omitted and the camera functionality of the mobile electronic device is used to capture the fluorescent images of the patterns 16.

Figure 9:
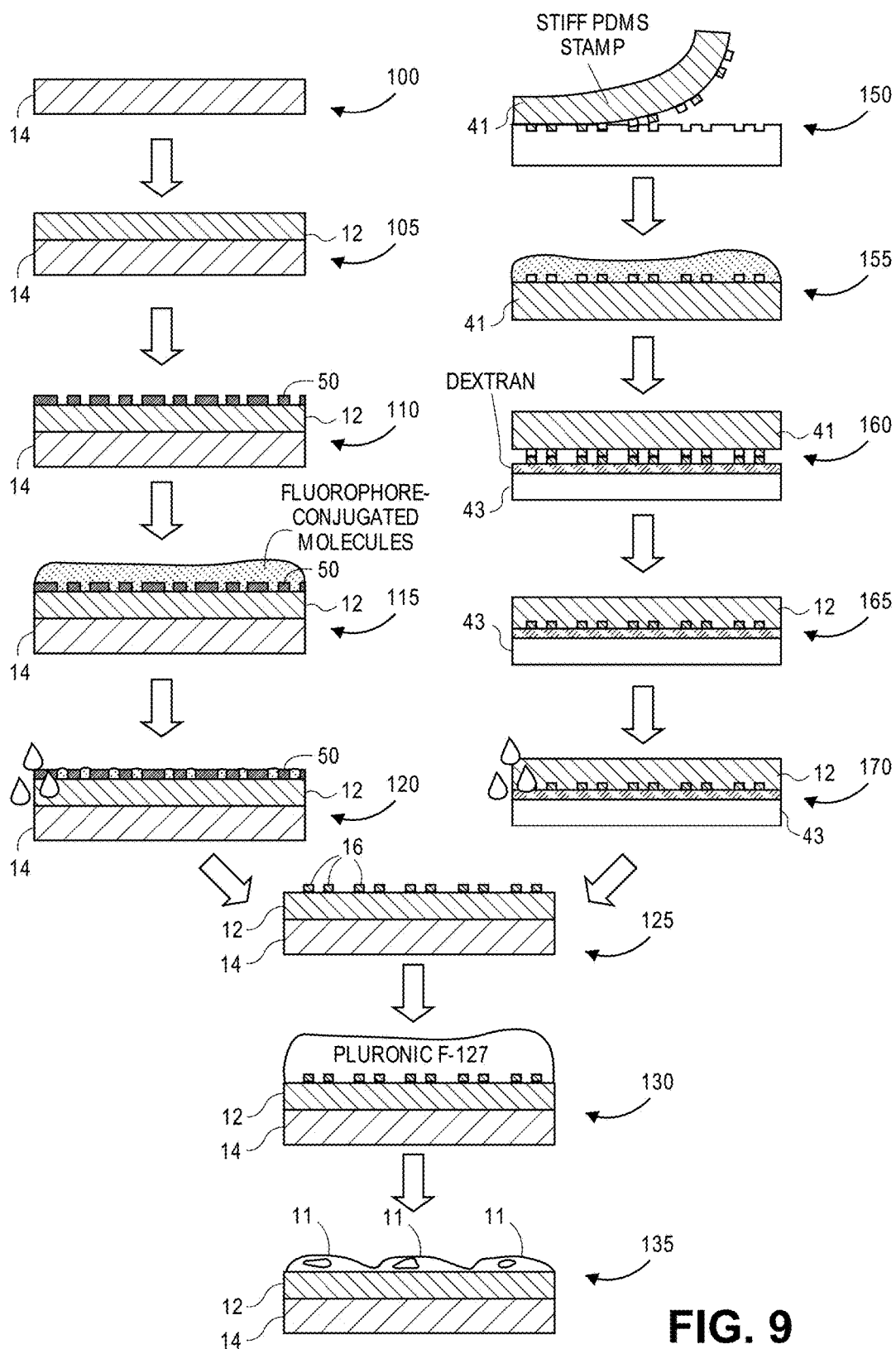
FIG. 9 illustrates the operations or steps of two different methods used to create the soft polymer layer atop the optically transparent layer having molecular patterns formed thereon.

FIG. 9 illustrates two different methods that can be utilized to form device structure that has the optically transparent substrate 14, the layer 12 of soft material, and the molecular patterns 16. These include an adsorption/lift-off method and a pattern transfer and incorporation method. The adsorption/lift-off method relies on non-specific adsorption of adhesive molecules used as part of the pattern 16 as a mechanism of molecule-to-substrate attachment. First, in operation 100 an optically transparent substrate 14 such as glass is provided and treated with oxygen plasma and exposed to allyltrimethoxysilane in vacuum for 12 hours. Next, as seen in operation 105, a thin film (e.g., less than about 20 microns in height) of soft PDMS having a Young's modulus upon curing within the range of about 3 kPa to about 100 kPa is spun on the optically transparent substrate. The softness is adjusted by controlling the ratio of base-crosslinker which should be in the range of about 50:1 to about 70:1 although numbers outside may work as well. In operation 110, a thin layer (<1 μm height) of positive photoresist 50 is spun (e.g., 30 seconds at 2400 RPM) onto the soft PDMS layer 12 and is exposed to UV light through a photomask, designed with software such as "L-Edit," with clear regions in the desired adhesive patterns 16. The photoresist 50 is developed and baked to create adhesive regions 16 on the PDMS layer 12. The selected adhesive molecules (e.g., fluorophore-conjugated molecules) are then allowed to non-specifically adsorb to the PDMS layer 12 as seen in operation 115. Next, as seen in operation 120, a lift-off process is performed using ~1 min of sonication and manual agitation in KOH developer to remove the remaining photoresist 50. The ultra-soft PDMS layer 12 is now formed as seen in operation 125 of FIG. 9 that includes the molecular patterns 16 formed thereon. The molecular patterns 16 preferably have a minimum line width of around 3 μm. As one example, molecular patterns 16 may be formed with fibrinogen-Alexa Fluor® 488 and human fibronectin arranged in crosses (50 μm diagonal, 10 μm line-width) spaced 25 μm apart.

In operation 130, the structure that includes the optically transparent substrate 14 and the PDMS layer 12 is treated with a pluronic solution (e.g., Pluronic F-127 <1% wt/vol) for 40 minutes to prevent non-specific adsorption of cells 11 off of the adhesive patterns 16 which would complicate data analysis following imaging. In operation 135, cells 11 are seeded onto the PDMS layer 12 containing the molecular patterns 16.

FIG. 9 also illustrates the pattern transfer and incorporation method that is used to prepare an optically transparent substrate 14 with an ultra-soft polymer layer 12 that has adhesive patterns 16 formed thereon. This method uses a pattern transfer and incorporation process. This method creates covalent bonds between the chosen adhesive molecule(s) and the soft PDMS layer 12. First, as seen in operation 150 soft lithography is used to create a stiff PDMS stamp 41 (10:1 base to crosslinker ratio used to form the stamp 41) containing the desired geometrically shaped and sized patterns.

To form the stamp 41 a photoresist master mold is fabricated, using software such as "L-Edit" to design a metal photomask with the desired patterns. Fabrication of the chrome photomask is outsourced. A positive photoresist such as SPR-220-7 (thick resist) is spin-coated onto a silicon wafer, soft baked, exposed through the metal (e.g., chrome) photomask, and developed until the master mold is ready. The mold is taped to a petri dish and 10:1 PDMS is poured over it and cured. The mold size ranges from ~1 in² (for small samples) to 9 in² squares for the well-plate embodiment. The sizing is arbitrary and easily scalable.

Once the stamp 41 is cleaned or otherwise treated, the chosen adhesive molecule(s) are then inked onto the stamp 41 as seen in operation 155. For example, a protein solution is pipetted onto the stamp 41, allowed to wet the entire surface, and covered with a plastic sheet cut to size to help the solution spread over the full surface and prevent drying. This adsorption reaction happens for 30-60 minutes depending on the protein used.

Once the adhesive molecule(s) have adsorbed to stamp 41, the stamp 41 is dried with pressurized air. Once dry the stamp 41 is immediately used to stamp the dextran-coated silicon wafer 43 as seen in operation 160. Dextran is purchased (Sigma-Aldrich) as a powder typically at the 70 kD-100 kDa sizes. A 20% mass-by-vol solution is prepared in deionized water in a test tube. The tube is mixed continuously (taped to a vortex mixer for example) for up to 30 minutes or until the dextran is fully dissolved. Silicon wafers are treated with plasma for 30 seconds to improve their hydrophilicity and the dextran solution is spin-coated onto the wafer to form a uniform sub-micron height coating. After spinning the dextran-coated wafers are baked at 150° C. for at least five (5) minutes to dry.

The stamping process includes rolling the stamp 41 with a cylindrical object along several directions to aid in transferring the adhesive and fluorescent molecules from the PDMS stamp 41 to the dextran-coated silicon wafer 43. After rolling, a set of glass slides can be used as a weight and applied on the stamp 41 and kept in place for several minutes. After transfer of the adhesive molecule(s) is complete, the weights can be removed and the stamp 41 is carefully removed from the dextran-coated wafer 43. Still referring to FIG. 9, as seen in operation 165 uncured ultra-soft PDMS is spun onto the dextran coated wafer.

The ultra-soft PDMS mixtures are prepared in 50 mL tubes (or other tapered, closed container for best mixing). Crosslinker is first weighed out, then the appropriate amount of base is added. Working ratios are generally 50:1 to 70:1 though this range may expand to, for example, 20:1 to 70:1 so the amount of crosslinker is very low, requiring one to use a closed container with preferably a tapered bottom that can be inverted and/or vortexed to promote optimal mixing. After inverting/vortexing for ~3 minutes, the PDMS mixture is placed in vacuum to remove air bubbles (approximately 1 hr). Within about two (2) hours of mixing the PDMS, the PDMS is spin-coated on the dextran-coated wafers that have been stamped with protein or other molecule to form the pattern 16. The target height is about 10-15 microns. This height range is optimal for the well-plate format in terms of bonding the well-containing plate 40 with the layer 12.

After the soft-PDMS mix is spin-coated onto the stamped dextran-coated wafers, the wafers are left on a flat surface at room temp overnight to allow even distribution of the polymer (equal height), then placed into an oven (60-80° C.) and cured until ready. The crosslinker used to polymerize the PDMS also acts to crosslink the transferred adhesive molecule(s) and thus covalently incorporates the molecule(s) into the PDMS surface of the PDMS-dextran interface. Finally, as seen in operation 170, the dextran is sacrificed (i.e., dissolved away) in water (or other solvent with high dextran solubility) which releases the thin-film PDMS layer 12 that incorporates thereon the molecular patterns 16. A razor blade may be used to cut away a small amount of the periphery of the PDMS layer 12 from the wafer to expose the dextran to solution. After the periphery of the PDMS layer 12 is cut away a glass backing layer that forms the optically transparent substrate 14 is then contacted with the PDMS layer 12 and light pressure applied to ensure good contact between the glass and the PDMS layer 12. After the glass backing is added, the sample is submerged in PBS solution. An optional shaker may be used to hasten the dissolving of the dextran layer. The dextran layer quickly dissolves and the glass-backed PDMS layer 12 floats freely in solution. The PDMS layer 12 and glass substrate which forms the optically transparent substrate 14 is then carefully removed and inverted to be glass side down until it is ready to be sterilized with a strong base. The process of the thin-film PDMS layer 12 being transferred and mounted to the optically transparent substrate 14 is illustrated in operation 125. The process proceeds as previously described with the addition of a pluronic solution and seeding of cells 11.

The pattern transfer and incorporation method described in the context of FIG. 9 is preferred and has been used to pattern a number of molecules onto the layer 12. These include, Fibronectin, Fibrinogen, Bovine Serum Albumin, Ovalbumin, Streptavidin, Collagen Type I, Collagen Type IV, Vitronectin, and IgG. The adsorption/lift-off method described in FIG. 9 has been used with Fibronectin, Fibrinogen, and IgG. This is due in part to the inability to treat soft PDMS with plasma as this creates a thin oxide layer than changes the mechanical properties of the sample. Other advantages of this pattern transfer approach include the covalent coupling of protein into the polymer matrix which prevents cell-induced breakage of patterns during high force generation. Dextran-coated wafers stamped with the adhesive and fluorescent molecules are robust and storable. These non-hydrogel patterned substrates can be stored without hydration or refrigeration (both prior to and after PDMS has been spun on, but before the dextran release step) for at least several months improving robustness and allowing a less costly supply chain.

Cells 11 in a suspension, which can consist of cell lines brought into suspension by trypsinization or cell scraping, or cells naturally found in suspension in body fluids (e.g., blood, pleural fluid, urine, cerebral spinal fluid, etc.) are applied to the treated substrate and incubated for a period of time (between about 15 minutes to about 6 hours) to adhere to the adhesive micro-patterns 16 and begin to apply force or otherwise change the dimensions of the fluorescent pattern 16. The cells 11 may be monitored in a live state or they may be fixed with 4% paraformaldehyde and imaged.

Experiments with Human Cells

The well-based embodiment described herein has been used to measured pattern contraction and force generation when screening primary human airway smooth muscle cells exposed to acetylcholine, enodthelin-1, and histamine, and shown relaxation of smooth muscle contraction with ML-7 and albuterol exposure. A 96 well plate implementation was used to for the high throughput screening of these compounds that modulate and or affect contractility of airway smooth muscle (ASM) cells. FIG. 11A illustrates the contraction of ASM cells that were exposed to acetylcholine, enodthelin-1, and histamine. ML-7 was also added after contraction and was shown to relax smooth muscle contraction. This is seen by the reduction in deflection amount that was measured after addition of myosin light chain kinase inhibitor ML-7 (+ML-7). The negative control is also illustrated (−ML-7). FIG. 11B illustrates the contraction of ASM cells in response histamine as well as the resulting relaxation in response to the addition of albuterol (+ Albuterol). These results illustrate that the system can be used in the high throughput screening of candidate drugs for the treatment of inflammatory disease states that lead to smooth muscle contraction such as asthma. Multiparameter force phenotyping can be used on ASMs to identify links between contractility and biomolecular content and organization, and potentially identify molecular signatures of contractile sub-populations with the most therapeutic importance for asthma and drug screening. A key mechanism to treat asthma is through modulation of the contraction and proliferation of airway smooth muscle cells. This platform enables the high-throughput phenotypic screening method that targets contractility. Compounds can be identified that ameliorate bronchoconstriction and act through orthogonal signaling pathways to the current successful β2-adrenergic receptor agonists that are part of the standard of care.

FIGS. 12A and 12B illustrate how the platform and method can be used to generate dose-response data for force phenotyping. In this experiment, HeLa cells were loaded into the well-based embodiment. Wells were loaded with different concentrations of the myosin II inhibitor blebbistatin. Deflection measurements were made at the different concentration levels. In addition, relaxation of the HeLa cells was also measured. As seen in FIG. 12A, an increased concentration of blebbistatin resulted in less deflection. A dose-response curve is also illustrated in FIG. 12B showing the percentage of relaxation as function of blebbistatin concentration.

Compatibility with Other Biological Studies

Broadly speaking, the system has applications in: (1) force phenotyping of cells (i.e., identifying cell sub-populations by unique adhesive and contractile phenotypes rather than immunofluorescence); (2) drug discovery relating to cell contractility, and (3) diagnostics of immune dysfunction or immune state. The implementation described above, for example, is useful for measuring inherent cell forces exerted through focal adhesions and provides a high-throughput method of phenotyping adherent mammalian cells based on the magnitudes of these forces. Specifically, this is a measure of how intrinsically contractile a given cell type is (i.e., its contractility). This assay is especially useful in tracking differentiation of stem cells and other progenitor cells, and may be helpful in identifying specific cell types within mixed populations. Other implementations of this system provide ways of assaying various other biological behaviors and responses to stimuli as noted below.

Ligand-Mediated Forces:

The system can analyze the response of a given cell type to different surface-bound ligands. Since the system allows for any protein or other molecule to be patterned on an ultra-soft layer 12, a cell type can be screened against any number of ligands and the force-response can be measured in a well-defined manner. This may be used to create tissue-like structures or otherwise provide guidelines for tissue engineering.

Contractility Changes in Disease:

The system can be used to effectively quantify the differences in contractility between cells harvested from healthy tissue or organs and those harvested from damaged or recovering tissues (scar tissue) or organs. For example, contractility of myofibroblast or cardiomyocytes taken from a heart after a myocardial infarction could be compared to their healthy counterparts. Drugs could then be screened that may restore healthy levels of contractility. Similarly, intestinal smooth muscle cells, uterine smooth muscle cells and mesangial cells from disease models which have abnormal contractility can be compared to healthy cells and drugs screened to restore healthy function (e.g., force level of contraction).

Immune Function:

The system can be used to assay the immune state of a given organism by measuring various immunological functions of leukocytes, e.g. phagocytic ability and contractile force of various phagocytes, and functions of lymphocytes, e.g. binding and contractile ability of T cells. This assay can be used to diagnose immune function in patients and/or organisms quickly and in a functional way.

Phagocyte Function:

By patterning known opsonins such as antibodies, complement proteins and other circulating proteins as well as apoptotic bodies, the different phagocytes comprising the immune system, e.g., monocytes, neutrophils, macrophages, among others can be tested for phagocytosing ability (quantifiable through analysis of pattern deformation and/or by measuring the amount of opsonins remaining after the phagocytes adhere and apply force to envelop the pattern). The forces applied are expected to vary as a function of leukocyte type, activation, and opsonin (yielding patterns that are disease specific, e.g., for applications in monitoring bacterial or viral infection, transplant rejection, or autoimmune conditions). Forces are expected to also scale with level of immune activity (e.g., immunosuppression vs. hyperactivity).

Lymphocyte Function:

The system can be used for comparing the applied forces and adherence of lymphocytes, such as T cells, taken from healthy patients to those taken from patients with autoimmune disease, e.g., chronic inflammatory disease. T cells taken from patients with systemic lupus erythematosus have been known to display stronger actin polymerization, as well as increased adhesion, both of which are behaviors that are measurable with this system.

Allergen Assay:

The system can be used to pattern a variety of common allergens and screen an individual's basophils and mast cells for an allergic response in the form of increased binding, and therefore pattern deformation, which would be expected if the cells were decorated with large numbers of allergen-specific IgE, which is characteristic of an allergy.

Strain Due to Formation of Bio-Structures:

The system can be used to investigate and quantify the strain induced by the formation of various bio-structures such as multicellular bacterial biofilms as a function of structure size and duration of existence. Drugs could be screened that interfere with contractility of the biofilm or tissue-like structure (e.g., granuloma) which may be therapeutically useful to disrupt the biofilm or disaggregate the granuloma. Additionally, spores produced by certain bacteria have been shown to exert differential strain on substrates that depends on environmental conditions. See, e.g., Chen et al., O. Bacillus spores as building blocks for stimuli-responsive materials and nanogenerators. Nat Nano 9, 137-141 (2014). This system can be used to make simple and statistically significant comparisons of these responses against many environmental stimuli and assist in the development of spore-based stimuli-responsive materials.

Contractile Force Dependence on Cell Polarity:

The system can be used to study the contractile forces cells apply to a substrate if constrained to highly asymmetric patterns, causing polarization, which could aide in investigating biological processes involving cell polarity such as differentiation, proliferation, and migration, all of which are critical for organism development and maintenance. Since dysregulation of cell polarity is implicated in developmental disorders as well as cancer, drugs can be screened that may help control cell polarizability.

Effects of Electrical Stimulation on Contractility:

It has been shown that certain cell types align and/or elongate in a direction perpendicular to the direction of an applied electric field. The system may be used to now study cell contractile responses to such external stimuli. These studies would be especially useful for quantifying the contractile forces of excitable cells (e.g., neural cells, cardiomyocytes, smooth muscle cells) as well as the rates at which they are applied and related characteristics (e.g., periodicity).

Role of Genes in Contractility:

The system can be used in coordination with gene-silencing tools such as RNAi and CRISPR gene-editing technology to help identify which genes are most responsible for cell contractility and elucidate the pathways through which multiple genes work together to control contractility. Since cancer progression may rely on increased cell contractility, particularly for its role in migration and remodeling of the extracellular matrix (ECM), the system may be used to identify possible drug targets (e.g., proteins encoded by genes found to be implicated in contractility of malignant cells).

Unlike traction force microscopy and elastomeric micro-post methods, which allow cells to adhere in uncontrolled, random and, therefore, irreproducible morphologies that make comparisons between experiments difficult, the system and method described herein precisely constrains cells to patterns designed by the user. Since the orientation, extent of spreading, and polarization of adhered cells may dictate their mechanical responses to stimuli, they are important variables that must be controlled for, and this is achieved with high reproducibility with the patterning methods described herein. The invention utilizes a novel approach for taking measurements of cell contractility by imaging and measuring the dimensions of the fluorescent patterns occupied by the cells rather than the cells themselves, which is the standard approach. Additionally, the new method we show of using a sacrificial dextran layer and molding the proteins within the elastomeric matrix leads to higher adhesive strength of the pattern to the elastomeric substrate compared to adsorption-based patterning, avoiding issues of cells pulling the pattern off the substrate when they contract. Furthermore, due to the well-defined target measurements, e.g., dimensions of patterns in pixels, custom-written automated software is used to parse through large volumes of data and measure the patterns with high accuracy (tested against manual pixel length measurements), leading to a high-throughput platform compared to other platforms that must image at higher magnification or before and after a treatment at each individual location.

The platform technology disclosed herein will have several potential markets. For example the approach can provide solutions to immune diagnostic problems (e.g., quickly diagnosing lupus, which is notoriously difficult to detect with current commercial diagnostic solutions), provide a drug screening platform for pharmaceutical testing, or serve as a research tool to characterize cell differentiation. Generally, cell contractility is important to several physiological processes (e.g., cardiac function, immune cell function, smooth muscle function in various organs) and its dysregulation is implicated in a variety of diseases. Current methods of quantifying cell contractility have limitations in objectivity of measurements, through-put, and normalization of test conditions (e.g., cell morphology and extent of cell-cell contact). Through the use of fluorescent adhesive molecules arranged in precise micro-patterns on the surfaces of highly flexible substrates, the invention provides a simple tool for making well-defined quantitative measurements of cell contractility while maintaining strict control over environmental conditions and cell orientation, spacing and spreading. As such, it presents a solution for screening agents that affect cell contractility and could be used discover drugs and genes that restore healthy levels of contractility.

While embodiments of the present invention have been shown and described, various modifications may be made without departing from the scope of the present invention. The invention, therefore, should not be limited, except to the following claims, and their equivalents.

What is claimed is:

1. A method of forming a substrate having an array of molecular patterns comprising fluorescent-conjugated patterns comprising:
   providing an optically transparent substrate;
   forming a layer of polydimethylsiloxane (PDMS) on the optically transparent substrate having a Young's modulus within the range of about 3 kPa to about 100 kPa;

patterning a photoresist on the layer of PDMS;
attaching fluorescent-conjugated molecules to the layer of PDMS patterned with the photoresist; and
removing the photoresist.

2. The method of claim 1, further comprising treating the layer of PDMS having the patterned fluorescent-conjugated molecules with a pluronic solution.

3. A method of forming a substrate having an array of molecular patterns comprising fluorescent-conjugated patterns comprising:
preparing a stamp having a desired array of patterns;
attaching a plurality of fluorescent-conjugated molecules to the array of patterns of the stamp;
pressing the stamp to transfer the molecular pattern onto a sacrificial layer spun on a flat substrate;
forming a soft layer of silicone polymer on the stamped sacrificial layer, where the silicone polymer layer has a Young's modulus within the range of about 3 kPa to about 100 kPa;
sacrificing the sacrificial layer to release the soft layer of silicone polymer; and
mounting the soft layer of silicone polymer on an optically transparent substrate.

4. The method of claim 1, wherein prior to forming a layer of polydimethylsiloxane (PDMS) on the optically transparent substrate, the optically transparent substrate is exposed to allyltrimethoxysilane.

5. The method of claim 1, wherein the layer of polydimethylsiloxane (PDMS) is less than about 20 micrometers in height.

6. The method of claim 1, wherein the patterned photoresist comprises an array of geometrically shaped molecular patterns.

7. The method of claim 6, wherein the array of geometrically shaped molecular patterns comprises symmetrical patterns.

8. The method of claim 6, wherein the array of geometrically shaped molecular patterns comprises asymmetrical patterns.

9. The method of claim 6, wherein the geometrically shaped molecular patterns have a minimum line width of around 3 μm.

10. The method of claim 1, wherein the patterned photoresist comprises an array of geometrically shaped molecular patterns of different shapes.

11. The method of claim 1, wherein the optically transparent substrate comprises a plurality of wells formed thereon.

12. The method of claim 1, wherein the optically transparent substrate comprises glass.

13. The method of claim 3, wherein the silicone polymer comprises polydimethylsiloxane (PDMS).

14. The method of claim 3, further comprising treating the soft layer of silicone polymer with a pluronic solution.

15. The method of claim 3, wherein the sacrificial layer comprises dextran.

16. The method of claim 3, wherein the height of the soft layer of silicone polymer on the stamped sacrificial layer is between about 10-15 micrometers.

17. The method of claim 3, wherein forming a soft layer of silicone polymer on the stamped sacrificial layer comprises crosslinking the fluorescent-conjugated molecules to the silicone polymer via covalent bonds.

18. The method of claim 3, wherein the fluorescent-conjugated molecules comprise proteins.

19. The method of claim 3, wherein the optically transparent substrate comprises glass.

* * * * *